United States Patent [19]

Shibahara et al.

[11] Patent Number: 4,929,633
[45] Date of Patent: May 29, 1990

[54] ACTINONIN DERIVATIVES HAVING PHYSIOLOGICAL ACTIVITIES

[75] Inventors: Seiji Shibahara, Machida; Yukiko Takahashi, Kawasaki; Yuji Matsuhashi, Yokohama; Mitsugu Hachisu, Yokohama; Shinichi Kondo, Yokohama; Tomio Takeuchi, Shinagawa; Takaaki Aoyagi, Fujisawa, all of Japan

[73] Assignees: Zaidan Hojin Biseibutsu Kagaku Kenkyu Kai; Meiji Seika Kaisha, Ltd., Tokyo, Japan

[21] Appl. No.: 203,888

[22] Filed: Jun. 8, 1988

[30] Foreign Application Priority Data

Jun. 11, 1987 [JP] Japan .................................. 62-144176

[51] Int. Cl.$^5$ ..................... C07C 207/08; A61K 31/40
[52] U.S. Cl. ...................................... 514/423; 548/540
[58] Field of Search ......................... 548/540; 514/423

[56] References Cited

U.S. PATENT DOCUMENTS

| | | | |
|---|---|---|---|
| 3,240,787 | 3/1966 | Singh et al. ..................... | 548/540 X |
| 4,663,342 | 5/1987 | Umezawa et al. ................. | 514/423 |
| 4,701,465 | 10/1987 | Tanaka et al. ................... | 548/540 X |
| 4,743,616 | 5/1988 | Tanaka et al. ................... | 548/540 X |

OTHER PUBLICATIONS

Gordon et al., C.A., 59247c, 83(1975).
Devlin et al., C.A., 59251z, 83(1975).
Devlin et al., C.A., 59252a, 83(1975).
"Journal of Antibiotics" 38, 1629–1630 (1985), Umezawa et al.
Japanese Patent Appln. first Publication, "Kokai", No. 15840/86 and English Abstract thereof, (1986).
Japanese Patent Appln. first Publication "Kokai", No. 4228/87 and English Abstract thereof, (1987).
"J.C.S. Perkin Transaction I", (1975), 819–825, Gordon et al.
"J.C.S. Perkin Transaction I", (1975), 846–851, Devlin et al.
"Studies Concerning the Antibiotic Actinonin. Part VIII. Structure–Activity Relationships in the Actinonin Series", 1975, 857–860, Broughton et al.

Primary Examiner—Joseph Paul Brust
Attorney, Agent, or Firm—Lalos & Keegan

[57] ABSTRACT

As new compounds are provided a class of derivatives of actinonin represented by the general formula

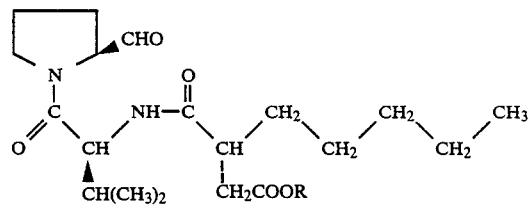

where R is a hydrogen or a lower alkyl group, which can exhibit the enzyme-inhibitory activities to a limited range of peptidases and show a remarkable enzyme-specificity, and which are effective to treat a cycloheximide-induced experimental amnesia in mice and are expectable to be useful to treat an amnesia in a mammalian animal, including human.

6 Claims, No Drawings

ACTINONIN DERIVATIVES HAVING PHYSIOLOGICAL ACTIVITIES

SUMMARY OF THE INVENTION

This invention relates to such new derivatives of actinonin which are obtained by chemical modification of a known compound, Actionin, and which show different physiological activities, especially an enzyme-inhibitory activity against a post-proline-cleaving enzyme (abbreviated as "PPCE") and also show therapeutic effects for treatment of an experimental amnesia in a mammalian animal such as mouse and may be expected to be useful in the therapeutic treatment of amnestic human patients. This invention also relates to processes for the preparation of such new actinonin derivatives as mentioned above. This invention further relates to a method of therapeutically treating amnesia in a mammalian animal. The known compound, actinonin is a metabolic product as produced by a certain strain of the microorganisms of Actinomycetes.

BACKGROUND OF THE INVENTION

Known metabolic products of microorganisms include a variety of organic compounds having different chemical structures and different physiological activities. The techniques which use the known metabolic products of microorganisms as antibiotics have been extensively investigated and utilized. We, the present inventors, have investigated physiological activities of these metabolic products having special chemical structure, in respect of their activities other than the antibacterial and antifungal properties so as to use the metabolic products of microorganisms as medical drugs other than the antibiotics. In the course of the series of our investigations, actinonin—the compound which had been described as an antibiotic having antibacterial activity in literature (for example, U.S. Pat. No. 3,240,787 Specification) and which is represented by the formula (II)

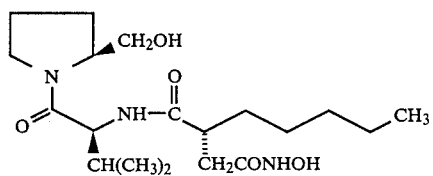

(II)

—was found to inhibit a wide variety of peptidases [see "Journal of Antibiotics", 38, 1629–1630 (1985)].

Besides, we discovered that actinonin has an immunopotentiating activity (see Japanese patent application first publication "Kokai" No. 15840/86 or U.S. Pat. No. 4,663,342) and that actinonin can inhibit the enkephalin-degrading enzymes and shows an anodyne activity (see Japanese patent application first publication "Kokai" No. 4228/87).

The previous syntheses of related compounds of actinonin have also been investigated for the limited purpose to improve the antibacterial activities of actinonin and are reported in the literature "Journal of the Chemical Society, Perkin Transactions I", 1975, page 846.

When actinonin is intentionally used as an enzyme-inhibitor against such enzymes which are produced by mammals including man, the inherent antibacterial activities of actinonin do not contribute to the enzyme-inhibitory effects of actinonin to be utilized and rather are an undesired property.

While, the previous investigations made for the purpose to synthetize the actinonin-related compounds have each been performed by a total synthetic process and hence have not provided industrial processes of preparing the actinonin-related compounds. According to an investigation made by the present inventors, it has been noted that the enzyme-inhibitory effects of actinonin are lacking the enzyme-specificity. Actinonin can therefore inhibit a wide range of enzymes and accordingly, has a problem that actinonin is not suitable for use as a medical drug for human.

We, the present inventors, have been proceeding with our investigations with a view toward producing such novel actinonin-related compounds, which are useful as a peptidase-inhibitor having a high enzyme-specificity, by using a fermentatively produced actinonin as a starting material for synthesis of actinonin-related compounds, and then effecting chemical modifications of actinonin. We have expected that the unsuitability of actinonin as a medical drug can be solved if we have succeeded in synthetizing such new actinonin-related compounds which are useful as a peptidase-inhibitor with a high enzyme-specificity. As stated hereinbefore, actinonin can exhibit the antibacterial activities and inhibit a wide range of substrates and a broad range of peptidases. For instance, actinonin shows a medium enzyme-inhibitory activities against two kinds of enzymes, namely, angiotensin-conversion enzymes (abbreviated as "ACE") and the above-described enzyme PPCE. We have now found that the removal of the hydroxyamino group present in the actinonin molecule which is essential for the development of the antibacterial activity of actinonin can provide a class of novel actinonin-related compounds which are represented by the general formula (I) given below and can inhibit only certain limited kinds of peptidases.

As a result of our investigations, we have now succeeded in synthetizing and providing a class of new actinonin-related compounds which are represented by the general formula (I) given below and which are inhibitory to the limited range of peptidases and are of a high enzyme-specificity.

DETAILED DESCRIPTION OF THE INVENTION

According to a first aspect of this invention, there is provided an actionin derivative represented by the general formula (I):

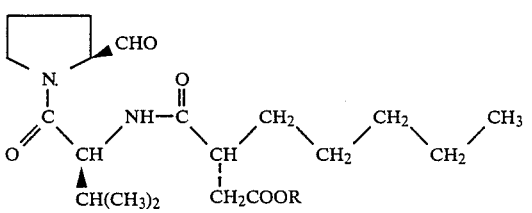

(I)

wherein R means a hydrogen atom or a lower alkyl group.

In the compound of the general formula (I), the lower alkyl group for R may be an alkyl group of 1–6 carbon atoms, with an alkyl group of 1–5 carbon atoms being preferred. Preferred examples of the lower alkyl group includes methyl, ethyl, propyl and isopropyl. The compound of the present invention, which is represented by the general formula (I), shows a strong PPCE-inhibiting activity but does have no enzyme-inhibitory activities against the enzyme ACE. The compound (I) of the present invention has therefore been found to exhibit such unique enzyme-specificity that, among the enzyme-inhibitory activities of actinonin against a wide range of peptidases, the enzyme-inhibitory activity of the actinonin against PPCE have been enhanced while the other enzyme-inhibitory activities of actinonin have been reduced or eliminated.

Further, as one of the physiological activities of the compound (I) of this invention, the compound of the formula (I) shows the therapeutic effects to therapeutically treat an experimental amnesia in mice. Hithertobefore, such compounds having the enzyme-inhibitory activity against PPCE have been studied as therapeutic drugs for various encephalopathy. Of these, the therapeutic effects of compounds for the amnesia can be tested in regard to the therapeutic effects of compounds for an experimental amnesia in mice which has been induced by administration of cycloheximide to mice. We have confirmed experimentally that the compounds of the formula (I) above according to this invention have such therapeutic effect which are able to reduce or eliminate a sympton of the cycloheximide-induced amnesia in mice.

The following particular compounds may be mentioned as illustrative examples of the compound of the formula (I) of this invention. (1) (2S)-2-Pentylsuccinyl-L-valyl-prolinal represented by the formula (Ia) [namely, Compound of Example 1 of this invention given hereinafter]:

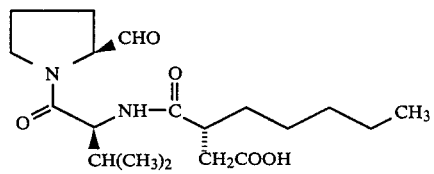
(Ia)

(2) (2S)-3-Ethoxycarbonyl-2-pentylpropionyl-L-valyl-L-prolinal represented by the formula (Ib) [namely, Compound of Example 2 of this invention given hereinafter]:

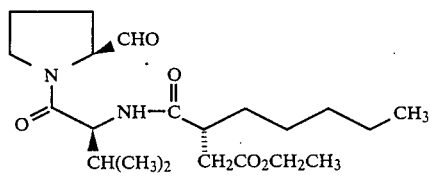
(Ib)

(3) (2S)-3-Methoxycarbonyl-2-pentylpropionyl-L-valyl-L-prolinal represented by the formula (Ic) [namely, Compound of Example 3 of this invention given hereinafter]:

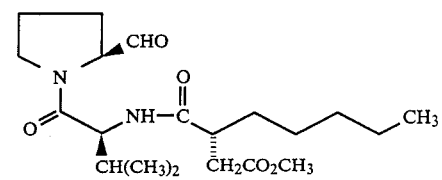
(Ic)

The compounds of the general formula (I) can each be produced by starting from actinonin of the formula (II) according to such processes which comprise the reaction steps as described below.

Incidentally, the starting compound, actinonin of the formula (II) itself is already known as described in U.S. Pat. No. 3,240,787 and can be obtained either by culturing a strain MG848-hF6 which is a strain of the genus Actinomycetes described in U.S. Pat. No. 4,663,342, or by culturing Streptomyces strain cutter C/2 (NCIB 8845) (ATCC No. 14,903) (see U.S. Pat. No. 3,240,787) in a known manner for the cultivation of strains of the genus Streptomyces.

Thus, the compounds of the general formula (I), including the compound of the formula (Ia) shown below and the compounds of the formula (I') shown below, may be produced by such processes comprising the reaction steps as depicted by the following reaction schemes A and B.

REACTION SCHEME A

Reaction Scheme A:

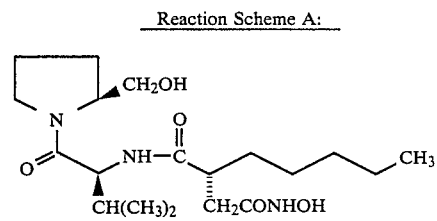
(II)

↓ (Hydrolysis of a hydroxamic acid)

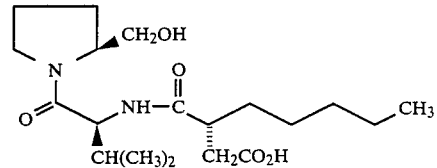
(III)

↓ (Oxidation)

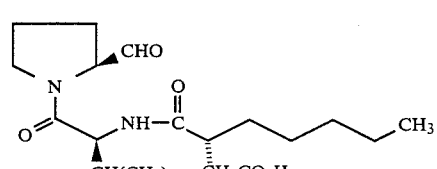
(Ia)

REACTION SCHEME B

Reaction Scheme B
Compound (III)

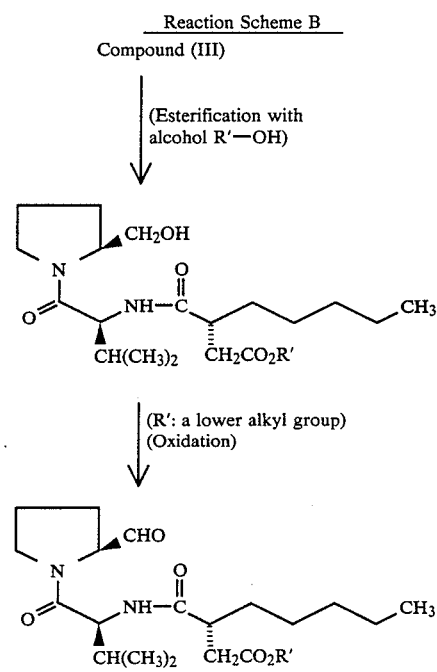

(IV)

(R': a lower alkyl group)
(Oxidation)

(I')

The individual reactions as shown in the above reaction schemes A and B will next be described.

Actinonin of the formula (II) is firstly suspended in water and then treated with an alkali metal periodate such as sodium periodate at ambient temperature so as to conduct the hydrolysis of a hydroxamic acid as indicated in Reaction Scheme A, whereby the hydroxyamino group is removed from the actinonin molecule to produce the succinic acid derivative of the formula (III). The hydroxymethyl group of the prolinol moiety present in the compound of the formula (III) is then oxidized into the formyl group (—CHO) to give the compound of the formula (Ia), namely the compound of the general formula (I) of this invention, where R is a hydrogen atom. This oxidation reaction may be carried out by any oxidizing method, so long as it is applicable comonly to oxidize an alkanol into its corresponding aldehyde. It is, however, preferable to use such an oxidation reaction which is known generally as "Pfitzner-Moffatt process", and in which dimethysulfoxide (DMSO) is used as the oxidant, in combination with an activating reagent therefor. Especially, the target compound of the formula (Ia) can be obtained in a high yield when the combination of DMSCO and a sulfur trioxidepyridine complex of the formula

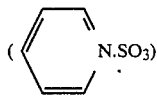

is reacted with the compound of the formula (III).

On the other hand, when the esterification of the succinic acid derivative of the formula (III) in the free carboxylic acid form is conducted by reaction with a desired alcohol of the formula (V)

R'—OH (V)

wherein R' means a lower alkyl group, as shown in Reaction Scheme B, the corresponding ester compound of the formula (IV) can be afforded. This esterification of the compound (III) can be effected in a usual manner known conventionally, for example, by reacting the succinic acid derivative (III) with the desired alcohol (V) of the formula R'—OH, wherein R' has the same meaning as defined above, and this esterification may preferably be conducted in the presence of an acid catalyst or a dehydrating and condensing agent, or it may comprise converting the compound (III) into an activated derivative such as an acid chloride or mixed acid anhydride and then treating the activated derivative with the desired alcohol of the formula (V). The ester compound (IV) can be obtained easily in a good yield when the compound (III) and the desired alcohol (V) are reacted with each other in the presence of 4-dimethylamino-pyridine and a dehydrating and condensing agent.

When oxidizing the ester compound (IV) in the same manner as in the oxidation of the compound of the formula (III), there can be obtained the compound of the formula (I'), which is a compound of this invention having the general formula (I), where which R' is a lower alkyl group such as ethyl, methyl or isopropyl group.

According to the second aspect of this invention, therefore, there is provided a process for the preparation of an actinonin derivative of the formula (Ia)

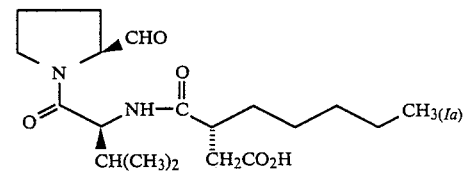

which comprises reacting actinonin of the formula (II)

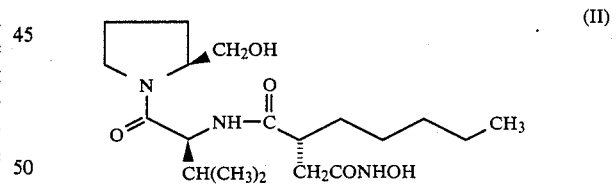

with an alkali metal periodate to remove the hydroxyamino group from the actinonin and thereby to give a compound of the formula (III)

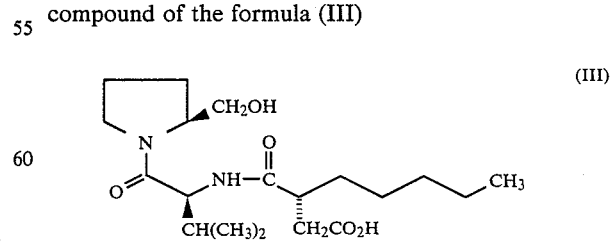

and then oxidizing the hydroxymethyl group of the prolinol moiety of the compound of the formula (III) into the formyl group to produce the compound of the formula (Ia).

According to the third aspect of this invention, there is also provided a process for the preparation of an actinonin derivative of the formula (I')

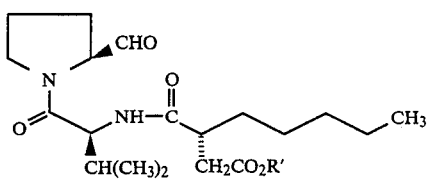
(I')

wherein R' means a lower alkyl group, which comprises reacting actinonin of the formula (II)

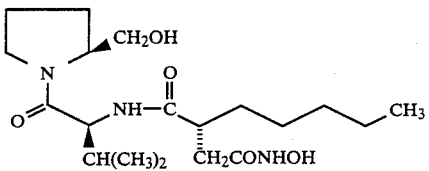
(II)

with an alkali metal periodate to remove the hydroxyamino group from the actinonin and thereby to give a compound of the formula (III)

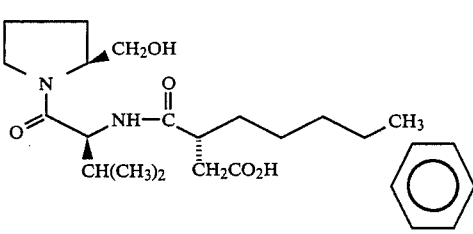
(III)

and esterifying the carboxyl group of the compound of the formula (III) by reaction with a lower alkanol of the formula (V)

R'—OH   (V)

wherein R' means a lower alkyl group to produce a compound of the formula (IV)

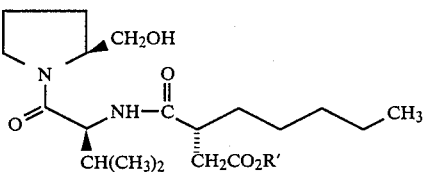
(IV)

wherein R' as defined above, and then oxidizing the hydroxymethyl group of the prolinol moiety of the compound of the formula (IV) into the formyl group to produce the compounds of the formula (I').

The compounds of the formulae (III) and (IV) which are produced as the intermediate products in the above processes are new compounds and are useful for the production of the actinonin-related compounds of the general formula (I) and also possibly for the synthetic production of any other actinonin-related compounds. The compounds of the formulae (III) and (IV) may be represented by the following general formula (VI)

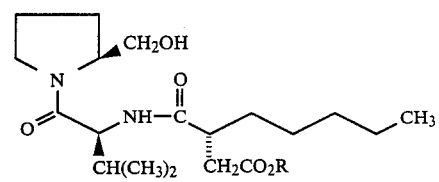
(VI)

wherein R means a hydrogen atom or a lower alkyl group.

Now, the physiological properties of the new compounds of the general formula (I) according to this invention are described.

(a) In order to demonstrate the enzyme-specificity as exhibited by the compounds of the formula (I) according to this invention, their enzyme-inhibitory activities against two kinds of peptidases, firstly, the angiotension-conversion enzyme (ACE) which contributes to the controlling of blood-pressure in mammalian animals, and secondly, the post-proline-cleaving enzyme (PPCE) which contributes to the mechanism of the memory in the brain of mammalian animals were estimated, as compared to the relative enzyme-inhibitory activities of actinonin as a reference compound.

The enzyme-inhibitory activities of these test compounds against PPCE were estimated by adding a substrate compound of the formula

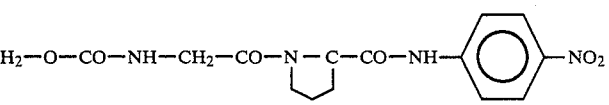

namely, N-benzyloxycarbonyl-glycyl-prolyl-p-nitroanilide (Z-Gly-Pro-PNA) to a solution of an enzyme, then adding to the solution each test compound having the enzyme-inhibiting activity to be assayed, reacting the substrate, the enzyme and the test compounds with each other at 37° C. for 15 minutes and then measuring the consumed amount of the substrate in terms of the determined reduction in the absorbency of a ultraviolet ray of a given wave length which transmitted the reaction solution where the substrate compounds, the enzyme and the enzyme-inhibiting test compound have been reacted with each other. In these tests, PPCE used was an enzyme preparation made from swine kidney and prior to its use, was purified by fractionation with ammonium sulfate and by subsequent chromatography on DEAE-Sephadex agent.

The enzyme-inhibitory activity of the test compounds against ACE were estimated in accordance with a method as described in the literature "Analytical Biochemistry", 84, 361 (1978). Results of the tests are shown in Table 1 below.

TABLE 1

Enzyme-Inhibitory Activities (in $IC_{50}$-value) of the Compound of the Invention

| Test compound | $IC_{50}$ (μg/ml) ACE-inhibitory activity | PPCE-inhibitory activity |
|---|---|---|
| Actinonin (as reference) | 14.6 | 30 |
| Compound of Example | >50 | 0.031 |

TABLE 1-continued

Enzyme-Inhibitory Activities (in IC$_{50}$-value) of the Compound of the Invention

| Test compound | IC$_{50}$ (μg/ml) ACE-inhibitory activity | PPCE-inhibitory activity |
|---|---|---|
| 1 of this invention | | |
| Compound of Example | >50 | 0.022 |
| 2 of this invention | | |
| Compound of the | >50 | >50 |
| Formula (III) | | |

As is apparent from the test results of Table 1, actinonin as the refrence compound shows a medium enzyme-inhibitory activity against the two enzymes, ACE and PPCE. On the other hand, the compounds of Example 1 and 2 of this invention which are the particular compounds of the formulae (Ia) and (Ib) according to this invention, exhibited a strong PPCE-inhibitory activity but had no enzyme-inhibitory activity against ACE. The new actinonin-related compounds of the formula (I) according to this invention can thus have an enhanced enzyme-inhibitory activity against PPCE but have a reduced or negligible enzyme-inhibitory activity agianst the other peptidases, in contrast to that actinonin can exhibit non-specific, some enzyme-inhibitory activities against a wide variety of peptidases. Accordingly, it has been revealed that the new actinonin-related compounds of the general formula (I) according to this invention are remarkably specific in exhibiting their enzyme-inhibitory activities.

(b) In order to demonstrate the other physiological activity of the new compounds of the formula (I) according to this invention that they exhibit the therapeutic effects to treat an experimental amnesia in mice, the therapeutic effects of the compounds of the formula (I) for such experimental amnesia of mice which is induced by administration of cycloheximide in mice were estimated in accordance with the experiments in which the step-down type passive avoidance response [see the "Journal of Pharmacological Methods" 16, page 39–52 (1986)] of tested mice was observed.

These experiments were performed using male ddy-mice having an average body weight of 25 g as the test animal. A platform in cubic form having a length of 4 cm for each side of the cube was arranged in a cage on the floor of the cage. Each mouse was placed on the platform. An electric current-feeding device had been provided on the floor area of the cage which positioned outside the platform. It was so arranged that whenever the mouse descended onto the floor from the platform, a 60 V electric current was caused to pass through the floor for 0.5 second to shock the mouse so as to have the mouse learn the shocking passage of electric current. Immediately after the mouse's learning, the mouse was subcutaneously administered with 30 mg/kg of cycloheximide so as to induce experimental amnesia. Each test compound had been intraperitoneally administered to the mouse at a time of 15 minutes before the mouse's learing was commenced. Upon an elapsed time of 24 hours after the completion of the mouse's learning for the electric current passage, the mouse treated as above was again placed on the same platform in the same cage under the same conditions, and the residence time of the mouse staying on the platform was measured under a pre-requisit that a maximum residence time as determined was set to be up to 300 seconds.

The results of the experiments for the cycloheximide-induced amnestic mice as treated by the previous intraperitoneal administration of the test compound of this invention are summarized in Table 2 below.

TABLE 2

Therapeutic Effects of Invention Compounds for Amnesia as Determined by Passive Avoidance Response Test of Mouse

| Mice treated with test compound indicated below | | Number of mice tested | Residence time (sec) |
|---|---|---|---|
| Control mice (not treated) | | 9 | 220 ± 37 |
| Mice treated with cyclo-heximide alone (Comparative) | | 10 | 114 ± 26 |
| Mice treated with cyclo-heximide + administered with 3 mg/kg or 10 mg/kg of compound of Example 2 of this invention | 3 mg/kg | 9 | 188 ± 35 |
| | 10 mg/kg | 9 | 180 ± 26 |

As is apparent from the results of Table 2, the compound of the formula (Ib) as obtained in Example 2 of this invention exhibited marked therapeutic effects to treat the experimental amnesia of the mice.

According to a further aspect of this invention, there is provided a method of treating an experimental amnesia in a mammalian animal, which comprises administering an actinonin derivative of the formula (I) as described hereinbefore, to the animal having the experimental amnesia, in an amount sufficient to reduce or eliminate a sympton of the amnesia.

According to another aspect of this invention, there is provided a method of treating an amnesia in an amnestic human patient, which comprises administering an actinonin derivative of the formula (I) as described hereinbefore, to the patient in an amount sufficient to reduce or eliminate a sympton of the amnesia.

According to further another aspect of this invention, there is provided use of the actinonin derivative of the formula (I) as a therapeutic agent for treating an amnesia in an amnestic human patient.

When the actinonin derivative of the formula (I) according to this invention is used as a therapeutic agent for treatment of amnesia, it may be formulated into various forms such as powder, tablet, capsule, injectionable solution or suspension, by mixing with a pharmaceutically acceptable solid or liquid carrier as usually known in the pharmaceutical field.

Now, this invention is illustrated with reference to the following Examples 1–4 which describe illustratively the processes for the production of the compound of the general formula (I) according to this invention.

EXAMPLE 1

Synthesis of (2S)-2-pentylsuccinyl-L-valyl-L-prolinol of the formula (III)

Actinonin (1.0 g) was suspended in water (100 ml), followed by addition of 15N aqueous sodium periodate (25 ml) to resulting aqueous suspension of actinonin. The suspension was then stirred overnight at room temperature so as to conduct the dehydroxyamination reaction, whereby the hydroxyamino group was removed from the actinonin molecule. The reaction mixture obtained was saturated with sodium chloride and then extracted with ethyl ether (100 ml). The resulting ethyl ether layer (i.e., the extract solution) was thereafter extracted twice with saturated aqueous sodium hydrogen carbonate (100 ml). The aqueous phases (the extract solutions) thus obtained were combined together and adjusted to pH 2 with 1N HCl. The resultant aqueous solution was saturated with sodium chloride and then extracted with ethyl ether (150 ml). The resulting extract solution in ethyl ether was dried over anhydrous sodium sulfate and filtered. The filtrate was concentrated to dryness, thereby affording the titled compound of the formula (III) as a colorless syrupy residue (790 mg).

Mass spectrum: m/z 370 (M+).
IR spectrum (in chloroform solution):
3300, 1600, 1650, 1580 cm$^{-1}$.
NMR spectrum (90 MHz, CDCl$_3$): δ 0.85 (9H, m, —CH$_3$×3), δ 1.2–1.6 (8H, m, —CH$_2$×4), δ 1.7–2.1 (5H, m, —CH$_2$×2, —CH×1), δ 2.2–2.9 (3H, m, —CH$_2$×1, —CH×1), δ 3.3–3.9 (4H, m, —CH$_2$×2), δ 4.3–4.7 (2H, m, —CH$_2$×2).

EXAMPLE 2

Synthesis of (2S)-2-pentylsuccinyl-L-valyl-L-prolinal of the formula (Ia)

The compound of the formula (III) (98 mg) obtained in the Example 1 and triethylamine (110 μl) were taken up in dry dimethylsulfoxide (1 ml), and to the resulting solution was added a solution (1 ml) of sulfur trioxidepyridine complex (124 mg) in dimethylsulfoxide, under stirring. The resultant mixture was stirred at room temperature for 15 minutes to conduct the reaction of oxidizing the hydroxymethyl group into the formyl group. The reaction mixture was thereafter poured into ice water (10 ml), followed by extraction with ethyl acetate (15 ml). The resultant organic layer (namely, the extract) was washed successively with water, saturated aqueous sodium hydrogen carbonate and water, was dried over anhydrous sodium sulfate, and was then filtered. The filtrate was concentrated to dryness. The residue was purified by chromatography on silica gel (developer solvent: a 10:1 mixture of chloroform and methanol), thereby giving the titled compound (Ia) as a syrupy residue (81 mg). TLC (silica gel):

Rf 0.5 (developer solvent: a 10:1 mixture of chloroform and methanol).
IR spectrum (in chloroform solution): 3300, 1720, 1690, 1650, 1580 cm$^{-1}$.
NMR spectrum (90 MHz, CDCl$_3$): δ 0.85 (9H, m, —CH$_3$×3), δ 1.2–1.6 (8H, m, —CH$_2$×4), δ 1.7–2.1 (5H, m, —CH$_2$×2, —CH×1), δ 4.3–4.7 (2H, m, —CH×2), δ 9.5 (1H, d, —CHO).

EXAMPLE 3

Synthesis of (2S)-3-ethoxycarbonyl-2-pentylpropionyl-L-valyl-L-prolinal of the formula (Ib)

(A) The compound of the formula (III) (100 mg) obtained in the Example 1 was dissolved in ethanol (2 ml). Under stirring the resulting solution, an ethanolic solution (1 mg) of DCC, i.e., dicyclohexylcarbodiimide (55 mg) was added thereto along with 4-dimethylaminopyridine (5 mg). The mixture thus-prepared was stirred overnight at room temperature to conduct the esterification of the compound (III) with ethanol. An insoluble matter, which had precipitated out, was filtered off, and the filtrate was concentrated under reduced pressure. The oily residue as formed was dissolved in ethyl acetate (15 ml). The resultant solution was washed successively with 2N HCl and water, and the organic layer thus formed was dried over anhydrous sodium sulfate. After filtering off the sodium sulfate, the filtrate was concentrated under reduced pressure. The crude product obtained as the residue was purified by silica gel chromatography on silica gel (developer solvent: a 3:1 mixture of chloroform and ethyl acetate), whereby the compound of the formula (IV) shown in the above reaction scheme B where R' was an ethyl group, namely, (2S)-3-ethoxycarbonyl-2-pentylpropionyl-L-valyl-L-prolinol (73 mg) was obtained.

TLC (silica gel):
Rf 0.4 (developer solvent: a 3:1 mixture of chloroform and ethyl acetate).

(B) The compound of the formula (IV) obtained, where R' was an ethyl group, was oxidized by reaction with dimethylsulfoxide in the presence of the sulfur trioxide-pyridine complex, in the same manner as in the Example 1, thereby affording the titled compound of the formula (Ib).

IR spectrum (in chloroform solution): 1720, 1710, 1655, 1605 cm$^{-1}$.
NMR spectrum (90 MHz, CDCl$_3$): δ 0.75–0.9 (12H, m, —CH$_3$×3), δ 1.2–1.6 (8H, m, —CH$_2$×4), δ 1.7–2.1 (5H, m, —CH$_2$×2, —CH×1), δ 4.05 (2H, q, —CH$_2$×2), δ 9.4 (1H, d, —CHO×1).

EXAMPLE 4

Synthesis of (2S)-3-methoxycarbonyl-2-pentylpropionyl-L-valyl-L-prolinal of the formula (Ic)

Following the procedure of Example 3, the compound (III) was esterified with methanol in the presence of dicyclohexylcarbodiimide to obtain its corresponding methyl ester [compound of the formula (IV), where R'=methyl]. This ester compound was thereafter oxidized by reaction with dimethylsulfoxide in the presence of the sulfur trioxide-pyridine complex, thereby obtaining the titled compound of the formula (Ic).

Mass spectrum: mz 383 (M++1).
IR spectrum (in chloroform solution): 3300, 1720, 1705, 1650, 1580 cm$^{-1}$.
NMR spectrum (90 MHz, CDCl$_3$): δ 0.75–0.9 (12H, m, —CH$_3$×3), δ 1.2–1.6 (8H, m, —CH$_2$×4), δ 1.7–2.2 (5H, m, —CH$_2$×2, —CH×1), δ 4.2 (3H, s, —CH$_3$×1), δ 9.4 (1H, d, —CHO×1).

We claim:

1. An actinonin derivative represented by the general formula (I):

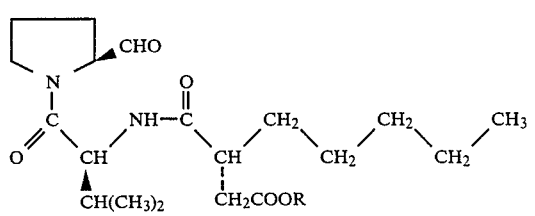

wherein R means a hydrogen atom or a lower alkali group.

2. The actinonin derivative as claimed in claim 1, wherein R is a hydrogen atom or a methyl or ethyl group in the formula (I).

3. A process for the preparation of an actinonin derivative of the formula (Ia)

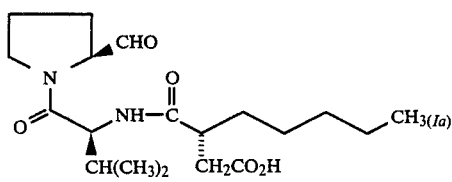

which comprises reacting actinonin of the formula (II)

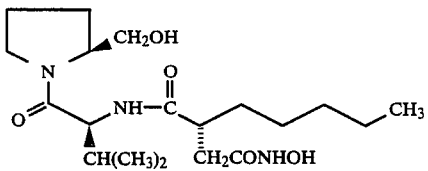

with an alkali metal periodate to remove the hydroxyamino group from the actinonin and thereby to a compound of the formula (III)

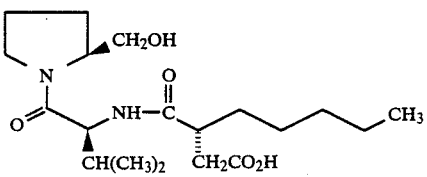

and then oxidizing the hydroxymethyl group of the prolinol moiety of the compound of the formula (III) into the formyl group to produce the compound of the formula (Ia).

4. A process for the preparation of an actinonin derivative of the formula (I')

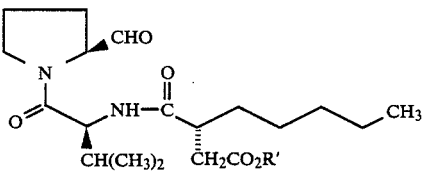

wherein R' means a lower alkyl group, which comprises reacting actinonin of the formula (II)

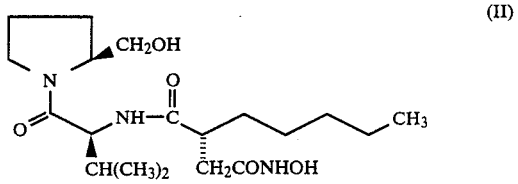

with an alkali metal periodate to remove the hydroxyamino group from the actinonin and thereby to give a compound of the formula (III)

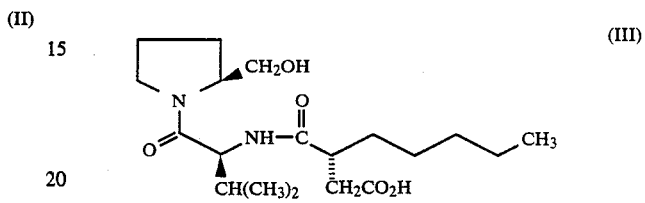

and esterifying the carboxyl group of the compound of the formula (III) by reaction with a lower alkanol of the formula

R'—OH  (V)

wherein R' means a lower alkyl group to produce a compound of the formula (IV)

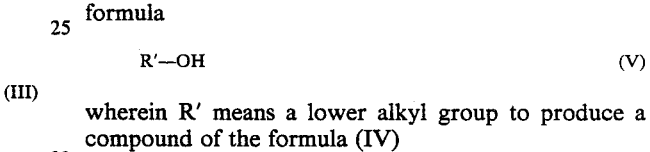

wherein R' is as defined above, and then oxidizing the hydroxylmethyl group of the prolinol moiety of the compound of the formula (IV) into the formyl group to produce the compound of the formula (I').

5. A method of treating an experimental amnesia in a mammalian animal, which comprises administering an actinonin derivative of the formula (I) as defined in claim 1, to the animal having the experimental amnesia, in an amount sufficient to reduce or eliminate a sympton of the amnesia.

6. A method of treating an amnesia in an amnestic human patient, which comprises administering an actinonin derivative of the formula (I) as defined in claim 1, to the patient in an amount sufficient to reduce or eliminate a sympton of the amnesia.

* * * * *